(12) United States Patent
Nevermann et al.

(10) Patent No.: US 7,208,453 B2
(45) Date of Patent: Apr. 24, 2007

(54) MEANS FOR INACTIVATING PATHOGENIC AGENTS ON SURFACES, INSTRUMENTS AND IN CONTAMINATED FLUIDS

(75) Inventors: Eugen Nevermann, Hamburg (DE); Jan Nevermann, Norderstedt (DE); Wolfgang Zerling, Kaltenkirchen (DE); Jutta Hoeffler, Hamburg (DE)

(73) Assignee: Menno Chemie-Vertrieb GmbH, Norderstedt (DE)

( * ) Notice: Subject to any disclaimer, the term of this patent is extended or adjusted under 35 U.S.C. 154(b) by 155 days.

(21) Appl. No.: 10/526,128

(22) PCT Filed: Sep. 20, 2002

(86) PCT No.: PCT/EP02/10583

§ 371 (c)(1),
(2), (4) Date: Jun. 20, 2005

(87) PCT Pub. No.: WO2004/021786

PCT Pub. Date: Mar. 18, 2004

(65) Prior Publication Data

US 2005/0239671 A1    Oct. 27, 2005

(30) Foreign Application Priority Data

Sep. 5, 2002   (DE) ............................... 102 40 985

(51) Int. Cl.
*C11D 3/48*   (2006.01)
*C11D 1/83*   (2006.01)

(52) U.S. Cl. ..................... 510/161; 510/382; 510/388; 510/421; 510/426

(58) Field of Classification Search ................ 510/161, 510/382, 388, 421, 426
See application file for complete search history.

(56) References Cited

U.S. PATENT DOCUMENTS

| 6,235,692 B1 * | 5/2001 | Scoville et al. ............. 510/160 |
| 6,294,186 B1 * | 9/2001 | Beerse et al. ................ 424/405 |
| 2005/0032913 A1 * | 2/2005 | McDonnell et al. ........ 514/731 |

FOREIGN PATENT DOCUMENTS

| DE | 1 288 747 | 2/1969 |
| WO | WO 94/17661 | 8/1994 |

* cited by examiner

*Primary Examiner*—Charles Boyer
(74) *Attorney, Agent, or Firm*—Bell, Boyd & Lloyd LLP

(57) ABSTRACT

The invention relates to ecologically-acceptable agent for treating pathogenic germs on surfaces, instruments and in fluids, comprising synergistic mixtures of aromatic hydroxybenzoic acids and phenols with a broad spectrum of action. The above is active against hydrophilically-sheathed and -unsheathed viruses as well as lipophilic bacteria and yeasts and is thus applicable in medicine, industry and commercial animal raising.

20 Claims, No Drawings

MEANS FOR INACTIVATING PATHOGENIC AGENTS ON SURFACES, INSTRUMENTS AND IN CONTAMINATED FLUIDS

BACKGROUND OF THE INVENTION

Infections acquired by patients in hospitals and other medical establishments cause great damage to the community of insured and to the national economy. These infections, called nosocomial diseases, have been attributed in the past, predominantly to bacteria.

SUMMARY OF THE INVENTION

On one hand, this has been due to the fact that in the absence of adequate medical diagnostics, many diseases having a mycological or viral genesis have not been recognized. On the other hand, infections caused by viruses and fungi have increased as a result of modern therapeutic measures and also as a result of travel and global interconnections; for instance, epidemics witnessed in more recent times in European animal husbandry such as mouth-and-foot disease, Aujeszky's disease, and swine fever, without any exception had a viral genesis. In hospitals, viral infections such as those due to the Norwalk-like viruses, rotaviruses, and adenoviruses, but also fungal infections leading to systemic mycoses and secondary infections, are diagnosed increasingly.

This new situation, and the new knowledge, have had the effect that in recent years, prophylactic measures such as procedures of disinfection must be reconsidered and conceived in a new way. Thus, a number of standardizing authorities demand that apart from bacteria, disinfection should also extend to particularly resistant fungi (e.g., *Aspergillus niger*) and viruses (e.g., poliovirus and adenovirus).

Disinfectants that are broadly applicable and have sufficient viricidal effectiveness are nowadays used in a very limited way only, the reason being side effects of the agents. This is particularly true for the aldehyde-type active agents, e.g., formaldehyde, glutaric dialdehyde, succinic dialdehyde, or glyoxal and their derivatives giving off aldehydes.

Up to now these components were regarded as the classical vectors of a broad antimicrobial and antiviral effectiveness in disinfectant formulations.

Formaldehyde and glutaric dialdehyde, which are the agents most universally applicable for fighting pathogenic agents owing to, amongst other reasons, the lack of technical problems in their application, have been classified as toxic and are suspected of being carcinogenic. Comparable characteristics are assumed to exist with the other aldehydes.

This causes users considering the potential risks to largely do without aldehyde-based disinfectants.

Other active agents that are available are not effective, or are only effective in a limited way, against unsheathed viruses and certain kinds of fungi, because of the particular resistance of these targets, or can only be used in a restricted way because of their unfavorable chemical and physical properties.

This holds true for the class of per compounds, for iodine, substances giving off chlorine, alcohols, cationic surfactants, amphoteric surfactants, phenols, bases, acids, and compounds giving off active oxygen.

The peracids for instance have a very highly diversified spectrum of antimicrobial action, but can be applied in a very limited way only owing to their extreme corrosivity. Considerable problems arise in addition from the lack of stability of this compound class.

While looking for an adequate alternative it has now been found surprisingly that the gap that had arisen may be closed when using certain mixtures consisting of aromatic hydroxycarboxylic acids and phenols, not only on account of the microbicidal effectiveness but also on account of the favorable toxicological and ecotoxicological properties and a favorable compatibility with materials.

Subject matter of the present invention are agents for the inactivation of pathogenic germs (bacteria, fungi, and viruses, sheathed and unsheathed) that can be applied to surfaces and instruments of all kinds as well as in contaminated fluids. The potential areas of application are the most diverse, e.g., in the context of hospitals, doctors' offices, production spaces of food industries and all the way to the stables of livestock breeders.

Additional features and advantages of the present invention are described in, and will be apparent from, the following Detailed Description of the Invention.

DETAILED DESCRIPTION OF THE INVENTION

A synergistic action between the components of the disinfectant mixtures according to the invention has been demonstrated, not only for the viricidal properties but also for the bactericidal and fungicidal properties. The enhancement of bactericidal and fungicidal action was all the more surprising inasmuch as for the phenols and aromatic hydroxycarboxylic acids used, excellent antimicrobial effects had already been known for the individual components.

Another remarkable feature is the unusual breadth of the spectrum of activity, which can be seen from the fact that the inactivation of hydrophilic Picorna viruses is just as reliable as the killing of lipophilic fungi.

The examples and tables reported in the following serve to explain the present invention and to prove the synergism between the synergists according to claim 1.

According to F. C. Kull and P. C. Eisman, *Applied Microbiology*, 9, 538–541 (1946), a synergism can be regarded as proven when a result of $F<1$ is calculated with the following formula:

$$F = QA/Qa + QB/Qb,$$

where the symbols have the meaning:

| | |
|---|---|
| $F < 1$ | Synergism |
| $F = 1$ | Additive effect |
| $F > 1$ | Antagonism |
| $Qa =$ | quantity of A alone to end point |
| $Qb =$ | quantity of B alone to end point |
| $QA =$ | quantity of A in the mixture with B |
| $QB =$ | quantity of B in the mixture with A. |

EXAMPLES

Example No. 1

| | |
|---|---|
| Alkyl aryl sulfonate Na | 12.0 parts by weight |
| Butyl monoglycol sulfonate Na | 5.0 |
| 4-Chloro-3-methylphenol | 15.0 |
| Phosphonobutanetricarboxylic acid | 1.5 |
| 2-Propyl alcohol | 30.0 |
| Water deionized | 36.5 |

Example No. 2

| | |
|---|---|
| Alkyl aryl sulfonate Na | 12.0 parts by weight |
| Butyl monoglycol sulfonate Na | 5.0 |
| 2-Hydroxybenzoic acid | 6.0 |
| Phosphonobutanetricarboxylic acid | 1.5 |
| 2-Propyl alcohol | 30.0 |
| Water deionized | 45.5 |

Example No. 3

| | |
|---|---|
| Alkyl aryl sulfonate Na | 12.0 parts by weight |
| Butyl monoglycol sulfonate Na | 5.0 |
| 4-Chloro-3-methylphenol | 15.0 |
| 2-Hydroxybenzoic acid | 6.0 |
| 2-Propyl alcohol | 30.0 |
| Phosphonobutanetricarboxylic acid | 1.5 |
| Water deionized | 30.5 |

Example No. 4

| | |
|---|---|
| Alkyl sulfonate Na | 10.0 parts by weight |
| Cumenesulfonate Na | 3.0 |
| 2-Phenylphenol | 15.0 |
| β-Resorcinolic acid | 7.0 |
| Formic acid | 5.0 |
| 2-Propyl alcohol | 33.0 |
| Water deionized | 27.0 |

Formulation Examples Nos. 1 to 3 were used to prove the synergistic effect concerning viricidal properies with the combinations according to the invention.

The unsheathed hydrophilic Picorna virus Polio Sabin LSc-2ab served as the test criterion. In the testing procedure and method, the rules of the preliminary European standard WI 216026 (phase2; step1) were followed.

Experimental Conditions:

| | |
|---|---|
| Temperature | 10° C. ± 1° C. |
| Contact time | 30 min ± 10 s |
| Protein load | 3 g bovine serum albumin and 10 g yeast extract per liter |

Unless pointed out otherwise, all numbers reported in the Table signify the infection titer (log $ID_{50}$, $ml^{-1}$) after a 30-min period of action; —means no longer detectable.

TABLE 1

(Polio Sabin)

| Sample | Control | Concentrations (%) 2% | 3% | 4% | 5% | 6% | 7% |
|---|---|---|---|---|---|---|---|
| Example No. 1 | 7.7 | 6.9 | 6.3 | 5.8 | 4.3 | 3.9 | 3.0 |
| Example No. 2 | 7.3 | 6.2 | 5.5 | 4.3 | 3.8 | 2.8 | 2.3 |
| Example No. 3 | 7.8 | 3.6 | 2.1 | — | — | — | — |

A result can be interpreted as sufficiently effective when the infection titer is reduced by four logarithmic steps, ie, when a 99.99% reduction of infectivity has been attained.

It follows from Table 1 that in Example 1, the phenol component was effective in an applied concentration of 7%, while in Example 2, the hydroxybenzoic acid had a sufficiently strong effect at a concentration of 6%. The mixture of the two components used in Formulation example No. 3 revealed a sufficiently strong inactivation of the poliovirus, already at a concentration of 2%.

Substituting these results into the formula of Kull and Eisman, we find:

$$F=2\times0.06/6\times0.06+2\times0.15/7\times0.15=0.62.$$

The numerical value of 0.62 thus yields unambiguous proof for the presence of a synergistic effect.

(Substituting the percent quantities of the active agents from the formulation examples into the equation produces a constant factor of 1, and hence is superfluous for the calculation.)

A synergistic effect in fungicidal effectiveness could be demonstrated in the instance of the particularly resistant *Aspergillus niger*.

The tests were conducted with the quantitative suspension test according to DIN EN 1650 (phase2; step1).

Experimental Conditions: DIN EN 1650

A germ count reduction by four logarithmic steps constitutes the required proof of effectiveness.

The test results are reported in Table 2. The numerical values given there are the logarithms ($\log_{10}$) of the reduced germ counts; the difference between these counts and the original germ count yields the reduction factor.

TABLE 2

(*Asp. niger*)

| Examples | Test solution log (germ count/ml) | Concentrations (%) 0.25% | 0.5% | 1% | 2% |
|---|---|---|---|---|---|
| 1 | 7.67 | 4.9 | 3.8 | 3.1 | |
| 2 | 7.67 | 5.2 | 4.2 | 2.8 | |
| 3 | 7.67 | 2.1 | | | |

$$F=0.25/1+0.25/1=0.50.$$

The above result of calculation from the data of Table 2 demonstrates that here, too, a synergistic effect of the mixture of active agents is present.

The proof for synergistically effective properties against bacteria was obtained in a quantitative suspension test according to DIN EN 1276 (phase2; step1) with a Gram-positive and a Gram-negative test organism.

Experimental Conditions: Period of Action: 20 min at 20° C. Protein Load: 3.0 g Bovine Serum Albumin Per Liter.

Table 3 shows the results obtained with *Escherichia coli*.

TABLE 3

(*E. coli*)

| | | Concentrations (%) | | | |
|---|---|---|---|---|---|
| Examples | Log (germ count/ml) | 0.25% | 0.5% | 1% | 2% |
| 1 | 8.49 | 4.63 | 4.1 | | |
| 2 | 8.49 | 5.15 | 4.9 | 2.9 | |
| 3 | 8.49 | 3.16 | | | |

$F=0.25/0.5+0.25/1=0.75$.

Table 4 shows the results obtained with *Staphylococcus aureus*.

Experimental Conditions: DIN EN 1276

TABLE 4

(*Staph. aureus*)

| | | Concentrations (%) | | | |
|---|---|---|---|---|---|
| Examples | Log (germ count/ml) | 0.25% | 0.5% | 1% | 2% |
| 1 | 8.4 | 5.9 | 4.8 | 3.3 | |
| 2 | 8.4 | 6.3 | 5.5 | 4.9 | 2.8 |
| 3 | 8.4 | 5.1 | 3.17 | | |

A germ count reduction by four logarithmic steps represented the required proof of effectiveness.

$F=0.5/1+0.5/2=0.75$.

The microbiological results needed to prove synergism could be obtained in all the tests, which demonstrates that the formulations according to claim 1 of the invention are synergistically effective against bacteria, fungi, and viruses.

The formulation according to Example No. 4 and the *Mycobacterium avium* Av 56 served to obtain proof of a tuberculocidal effect in the germ carrier test. The test conditions matched the provisions of the German Veterinary-Medical Society for the Area of Animal Husbandry (2$^{nd}$ edition 1998).

Germ carrier: sterilized limewood pieces (height 3 mm, length 10 mm, width 10 mm).

TABLE 5

(*Mycobacterium avium*)

| Example No. 4 | Period of action [min] | | | | |
|---|---|---|---|---|---|
| Concentration [%] | 30 | 60 | 120 | 180 | 240 |
| 2 | + | + | + | + | + |
| 4 | + | + | − | − | − |
| 5 | + | + | − | − | − |
| 6 | + | + | − | − | − |
| Formalin 3% | + | + | − | − | − |
| Growth control | + | + | + | + | + |

The test result presented in Table 5 shows that a 4% solution of Formulation example No. 4 after a period of action of 120 min yields the same effect as a 3% solution of Formalin. According to DAB 10 (German Pharmacopoeia 10$^{th}$ edition), Formalin contains 35 to 37% formaldehyde in water and 10% methanol, which corresponds to an effective concentration of about 1.1% aldehyde.

In the formulation according to Example No. 4, 15%+7% of an effective mixture of substances are present, of which 4% are employed, which corresponds to an effective concentration of the active agent of only 0.88%.

Formalin is the generally recognized reference and scale in germ carrier tests on limewood, since the relatively small aldehyde molecule will particularly well penetrate into the fissured and disintegrated fiber structure of the limewood carrier, and act there.

The result of the tuberculocidal effectiveness test underlines, just like the other results, that the present invention meets all conditions for being able to replace aldehyde-based disinfectant formulations.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. A method for the control and inactivation of pathogenic germs on surfaces and instruments of medical and technical establishments comprising the step of contacting the surface or instrument with a disinfectant composition comprising:
   an effective microbicidal and antiviral combination of
   A) at least one acid selected from the group consisting of aromatic monohydroxycarboxylic acids, dihydroxybenzoic acids, trihydroxybenzoic acids and mixtures thereof,
   B) phenols; and
   C) one or more surfactants selected from the group consisting of
      i) an anionic surfactant selected from the group consisting of alkyl sulfonates, alkyl aryl sulfonic acid, alkyl aryl sulfonates, alkyl aryl ether sulfates with 1 to 3 EO groups, alkyl ether sulfates with 1 to 3 EO groups, their sodium, potassium, and ammonium salts with primary or branched chains having a length of $C_8$ to $C_{18}$ and mixtures thereof; and
      ii) a nonionic surfactant selected from the group consisting of alkyl polyethyleneglycol ethers with 3 to 11 EO groups and mixtures thereof,
   wherein the weight ratio of component (C) to components (B+A) is between 1:9 and 9:1 and their sum is between 10 and 60%, referring to the total weight of the concentrated disinfectant formula.

2. The method according to claim 1, wherein the disinfectant composition further comprises at least one component selected from the group consisting of:
   i) a hydrotropic agent selected from the group consisting of butyl monoglycol sulfate, cumenesulfonate, toluenesulfonate, xylenesulfonate, their sodium, potassium, or ammonium salts thereof, and mixtures thereof;
   ii) a solvent selected from the group consisting of aliphatic alcohols, glycols having a chain length of C.sub.2 to C.sub.12, or mixtures thereof; and
   iii) a pH regulator selected from the group consisting of aliphatic carboxylic acids, hydroxycarboxylic acids having a chain length of C.sub.1 to C.sub.6, or mixtures thereof.

3. The method according to claim 2 wherein the weight of the hydrotropic agents and their salts, individually or in their mixture, is between 5 and 40% by weight, referring to the total weight of the disinfectant composition.

4. The method according to claim 2 wherein the weight of the alcohols, individually or in their mixture, is between 5 and 60% by weight, referring to the total weight of the disinfectant composition.

5. The method according to claim 1 wherein the disinfectant composition further comprises between 1 and 8% by weight of at least one sequestering agent selected from the group consisting of aminoacetic acids, phosphonic acids, their derivatives and mixtures thereof.

6. The method according to claim 1 wherein the antiviral combination is in an aqueous, dilute solution containing between 0.5 and 10% by weight of the disinfectant composition.

7. The method according to claim 1 wherein the phenols are selected from the group consisting of 2-isopropyl-5-methylphenol, 2-, 3-, or 4-methylphenol, hexylresorcinol, 2-phenylphenol, 2-methoxyphenol, 3-methyl-4-chlorophenol, 3,5-dimethyl-4-chlorophenol, 2-benzyl-4-chlorophenol, and mixtures thereof.

8. The method according to claim 1 wherein the aromatic monohydroxycarboxylic acid is selected from the group consisting of 2-; 3-; 4-hydroxybenzoic acid and mixtures thereof.

9. The method according to claim 1 wherein the dihydroxybenzoic acids are selected from the group consisting of 2,3-; 2,4-; 2,5-; 2,6-; 3,4-; and 3,5-dihydroxybenzoic acid and mixtures thereof.

10. The method according to claim 1 wherein the trihydroxybenzoic acid is selected from the group consisting of 2,3,4-trihydroxybenzoic acid, 2,4,6-trihydroxybenzoic acid, 3,4,5-trihydroxybenzoic acid and mixtures thereof.

11. A method of preparing a product for use as a disinfectant for the control and inactivation of pathogenic germs comprising the steps of producing a mixture comprising:
an effective microbicidal and antiviral combination of
A) at least one acid selected from the group consisting of aromatic monohydroxycarboxylic acids, dihydroxybenzoic acids, trihydroxybenzoic acids and mixtures thereof,
B) phenols; and
C) one or more surfactants selected from the group consisting of
 i) an anionic surfactant selected from the group consisting of alkyl sulfonates, alkyl aryl sulfonic acid, alkyl aryl sulfonates, alkyl aryl ether sulfates with 1 to 3 EO groups, alkyl ether sulfates with 1 to 3 EO groups, their sodium, potassium, and ammonium salts with primary or branched chains having a length of $C_8$ to $C_{18}$ and mixtures thereof; and
 ii) a nonionic surfactant selected from the group consisting of alkyl polyethyleneglycol ethers with 3 to 11 EO groups and mixtures thereof,
wherein the weight ratio of component (C) to components (B+A) is between 1:9 and 9:1, and their sum is between 10 and 60%, referring to the total weight of the concentrated disinfectant formula.

12. The method according to claim 11, wherein the disinfectant composition further comprises at least one compound selected from the group consisting of:
a salt selected from the group consisting of butyl monoglycol sulfate, cumenesulfonate, toluenesulfonate, xylenesulfonate as sodium, potassium, or ammonium salt and mixtures thereof;
one or more aliphatic alcohols or glycols having a chain length of $C_2$ to $C_{12}$; and
a pH regulator comprising one or more aliphatic carboxylic acids or hydroxycarboxylic acids having a chain length of $C_1$ to $C_6$.

13. The method according to claim 11 wherein the weight ratio of the component (A) to component (B) is between 1:9 and 9:1.

14. The method according to claim 11 wherein the disinfectant composition further comprises between 1 and 8% by weight of at least one sequestering agent.

15. The method according to claim 11 comprising the step of preparing an antiviral combination containing between 0.5 and 10% by weight of the disinfectant composition.

16. The method according to claim 11 wherein the phenols are selected from the group consisting of 2-isopropyl-5-methylphenol, 2-, 3-, or 4-methylphenol, hexylresorcinol, 2-phenylphenol, 2-methoxyphenol, 3-methyl-4-chlorophenol, 3,5-dimethyl-4-chlorophenol, 2-benzyl-4-chlorophenol, and mixtures thereof.

17. The method according to claim 11 wherein the aromatic monohydroxycarboxylic acid is selected from the group consisting of 2-; 3-; 4-hydroxybenzoic acid and mixtures thereof.

18. The method according to claim 11 wherein the dihydroxybenzoic acids are selected from the group consisting of 2,3-; 2,4-; 2,5-; 2,6-; 3,4-; and 3,5-dihydroxybenzoic acid and mixtures thereof.

19. The method according to claim 11 wherein the trihydroxybenzoic acid is selected from the group consisting of 2,3,4-trihydroxybenzoic acid, 2,4,6-trihydroxybenzoic acid, 3,4,5-trihydroxybenzoic acid, and mixtures thereof.

20. A method for the control and inactivation of pathogenic germs on surfaces and instruments of medical and technical establishments comprising the step of contacting the surface or instrument with a disinfectant composition comprising:
an effective microbicidal and antiviral combination of
A) at least one acid selected from the group consisting of aromatic monohydroxycarboxylic acids, dihydroxybenzoic acids, trihydroxybenzoic acids and mixtures thereof,
B) phenols; and
C) one or more surfactants selected from the group consisting of
 i) an anionic surfactant selected from the group consisting of alkyl sulfonates, alkyl aryl sulfonic acid, alkyl aryl sulfonates, alkyl aryl ether sulfates with 1 to 3 EO groups, alkyl ether sulfates with 1 to 3 EO groups, their sodium, potassium, and ammonium salts with primary or branched chains having a length of $C_8$ to $C_{18}$ and mixtures thereof; and
 ii) a nonionic surfactant selected from the group consisting of alkyl polyethyleneglycol ethers with 3 to 11 EO groups and mixtures thereof,
wherein the weight ratio of component (C) to components (B+A) is between 1:9 and 9:1, and their sum is between 5 and 40%, referring to the total weight of the concentrated disinfectant formula.

* * * * *